United States Patent [19]

Sanders

[11] 4,215,993

[45] Aug. 5, 1980

[54] PRECIPITATING REAGENT AND METHOD FOR ISOLATION AND DETERMINATION OF HIGH DENSITY LIPOPROTEINS IN HUMAN SERUM

[75] Inventor: James L. Sanders, Arlington, Tex.

[73] Assignee: Data Medical Associates, Inc., Arlington, Tex.

[21] Appl. No.: 966,145

[22] Filed: Dec. 4, 1978

[51] Int. Cl.$^2$ .......................................... G01N 33/16
[52] U.S. Cl. .................................. 23/230 B; 252/408
[58] Field of Search ...................... 23/230 B; 252/408; 260/112 B

[56] References Cited

U.S. PATENT DOCUMENTS

| | | | |
|---|---|---|---|
| 3,770,631 | 11/1973 | Fekete et al. | 260/112 B X |
| 3,955,925 | 5/1976 | Proksch et al. | 23/230 B |
| 4,086,218 | 4/1978 | Shanbrom et al. | 260/112 B |
| 4,110,077 | 8/1978 | Klein et al. | 23/230 B |
| 4,126,416 | 11/1978 | Sears | 23/230 B |

FOREIGN PATENT DOCUMENTS

2265121 5/1976 Fed. Rep. of Germany .... 195/103.5 R

*Primary Examiner*—Arnold Turk
*Attorney, Agent, or Firm*—Richards, Harris & Medlock

[57] ABSTRACT

A precipitating reagent and method is provided for isolating high density lipoproteins from low density lipoproteins in human serum together with a quantitative determination of high density lipoprotein cholesterol. Precipitation of low density lipoproteins is accomplished by the precipitating reagent without the addition of metal ions into the sample. The precipitating reagent lowers the pH of the human serum approximately to the isoelectric point of the low density lipoproteins through the use of an organic buffer. The precipitating reagent also contains a polyanion and neutral polymer. The preferred composition of the precipitating reagent contains about 0.4% phosphotungstic acid by weight thereof, about 2.5% of polyethylene glycol by weight thereof and 2-(N-morpholino) ethane sulfonic acid as the buffer present in a concentration of from about 0.2 molar to about 0.5 molar. According to the method provided, the precipitating reagent is added to the human serum sample thereby causing the low density lipoproteins to form a precipitate, leaving the high density lipoproteins in the resulting supernatant liquid. The supernatant is separated from the precipitate and a cholesterol assay reagent is added to the supernatant. The cholesterol assay reagent reacts with the high density lipoprotein to produce a compound that absorbs radiation at a specific wavelength. The amount of high density lipoprotein cholesterol present in the human serum sample is then determined by comparing the absorbance of a sample with the absorbance of a known standard.

24 Claims, No Drawings

PRECIPITATING REAGENT AND METHOD FOR ISOLATION AND DETERMINATION OF HIGH DENSITY LIPOPROTEINS IN HUMAN SERUM

BACKGROUND OF THE INVENTION

This invention relates to the selective separation of high density lipoproteins from low density lipoproteins in human serum. Another aspect of this invention relates to the selective precipitation of low density lipoproteins from human serum using a reagent which contains no divalent metal ions. Still another aspect of this invention relates to a method for separating high density lipoproteins from low density lipoproteins in human serum and quantitatively determining the high density lipoprotein components present in human serum.

For many years now, the medical profession has been concerned with the quantity of cholesterol present in human serum. Total serum cholesterol analysis has proven useful in the diagnosis of hyperlipoproteinemia, atherosclerosis, and hepatic and thyroid diseases. In the past, high cholesterol levels in human serum were linked to coronary heart disease and physicians often prescribed drugs to remove or greatly reduce cholesterol serum levels. Cholesterols or lipoproteins can be divided into two classes of related, though not identical, molecules. Although these fractions are not homogenous, their chemical and physical properties and metabolic interrelationships indicate that they do represent distinct classes of related molecules rather than arbitrary fractions defined by methods used in their isolation. Recently, it has been established that an inverse relationship exists between serum high density lipoproteins (high density cholesterol) and the risk of coronary heart disease. It has been further determined that the low density lipoproteins (low density cholesterol) deposit plaque on the inside of arteries whereas the high density lipoproteins actually dissolve plaque on the inside of the arteries. Thus, an accurate, reproducible and dependable in vitro quantitative test is important in diagnostic medicine because of the beneficial effects of high density lipoproteins and the harmful effects of low density lipoproteins. High density lipoprotein analysis is especially important for the assessment of coronary heart disease risk in apparently normal individuals.

In the past, low density lipoproteins have been precipitated with sodium phosphotungstate and magnesium chloride; with sulfated polysaccharides at a neutral pH; with polysaccharides of high molecular weight at a neutral pH; and with lower molecular weight polysaccharides, such as heparin in the presence of divalent cations. These methods are disclosed in Cornwell, D. G., and F. A. Kruger, 1961, *J. Lipid Res.* 2:10, and Burstein, M., H. R. Scholnick and R. Morfin, 1970, *J. Lipid Res.* 11:583. Another method used to separate high density lipoproteins is ultracentrifugation which can be slow and cumbersome.

Problems can occur in practicing these methods of separating high density lipoproteins from low density lipoproteins, especially in quantitative determinations. For example, previous quantitative methods have been based on metal polyanion precipitation including such combinations as divalent manganese cations plus heparin, divalent magnesium cations plus sodium phosphotungstate and divalent calcium cations plus dextran sulfate. The presence of metal cations causes interference in the subsequent cholesterol enzymatic assay. Further, higher concentrations of polyanions were previously required which inhibited the enzymatic cholesterol assay, preventing accurate and reproducible determinations of high density lipoprotein components. Also, previous precipitation methods were time and temperature dependent.

Thus, a need exists for a precipitating reagent and method using a low concentration of polyanions without metal ions to avoid inhibition of the cholesterol assay, which is accurate, reproducible and not time or temperature dependent.

SUMMARY OF THE INVENTION

According to the invention, a precipitating reagent and method for separating high density lipoproteins from low density lipoproteins and a method of quantitative determination for high density lipoprotein cholesterol is provided. The precipitating reagent for selectively precipitating low density lipoproteins from human serum contains phosphotungstic acid, an organic buffer having a pH range of from about 4.8 to 5.8 and a concentration of from about 0.2 molar to about 1.2 molar and a neutral polymer such as polyvinylpyrrolidone or polyethylene glycol. Preferably, the precipitating reagent contains about 0.4% phosphotungstic acid by weight thereof, 2-(N-morpholino) ethane sulfonic acid as the buffer, and about 2.5% polyethylene glycol having a molecular weight of about 6,000 by weight thereof. According to the invention, the precipitating reagent is added to a human serum sample resulting in a precipitate and supernatant fluid. The precipitating reagent lowers the pH of the serum to approximately the isoelectric point of the low density lipoproteins and causes their precipitation without the precipitation of high density lipoproteins. The supernatant fluid is separated from the precipitate. The precipitate contains low density lipoproteins and the supernatant contains high density lipoproteins. To the supernatant is added a reagent that causes an enzymatic reaction to take place with the high density lipoprotein cholesterol that produces a substance which absorbs radiation at a particular wavelength. After the enzymatic reaction takes place, the absorbance of the supernatant is determined and compared with the absorbance of a calibrated reference sample.

The precipitation reagent and method is not time or temperature dependent, is accurate and reproducible. In addition, no metal ions are introduced and a low concentration of polyanions is employed thereby preventing interference with the subsequent cholesterol assay.

DETAILED DESCRIPTION OF THE INVENTION

The precipitating reagent of the subject invention contains a polyanion, an organic buffer having a pH range of from about 4.8–5.8 present in a concentration of from about 0.2 molar to about 1.2 molar and a neutral polymer.

The preferred buffer of the subject invention is 2-(N-morpholino) ethane sulfonic acid (MES). MES is a zwitterionic buffer having a pKa of about 6.15 at 20° C. and a useful buffering range from about pH 5.2 to 6.8. Although the preferred buffer is MES, the precipitating reagent of the subject invention works effectively with a buffer having a pH range of 4.8 to 5.8 present in a concentration of 0.2 to 1.2 molar. For example, buffers such as citrate, having a pKa of about 5.40 at 20° C., and succinate, having a pKa of about 5.57 at 20° C. are suitable for use according to the invention. For effective precipitation of low density lipoproteins the final serum pH should be under 5.8, preferably at or near the isoelectric point of the low density lipoproteins. The buffer is used to lower the pH of the serum to approximately the low density lipoprotein isoelectric point and the concentration of the buffer must be such that this occurs. Use of a zwitterionic buffer offers advantages over conventional ionic buffers because metal binding properties and interference with the enzymatic cholesterol assay are minimized.

The preferred polyanion is phosphotungstic acid having a molecular weight of about 6,000 grams per mole. The phosphotungstic acid concentration should be present in the range from about 0.2% to about 3.0% by weight of the precipitating reagent. The preferred concentration of phosphotungstic acid is about 0.4% by weight of the precipitating reagent. Thus, the invention allows the use of low concentrations of phosphotungstic acid to prevent interference of the cholesterol assay by the polyanion.

According to the invention, use of the neutral polymer allows for a lower polyanion concentration in the precipitation of the low density lipoproteins thereby minimizing interference with the enzymatic cholesterol reaction by the polyanions. The preferred neutral polymers are polyvinylpyrolidone (PVP) and polyethylene glycol (PEG) with PEG being the most preferred neutral polymer. Another neutral polymer which may be used in accordance with the invention is poly-N-vinyl-5-methyl-2-oxazolidinone, sold by Dow Chemical under the trade name "Devlex."

According to the invention, the preferred molecular weight of the PVP is about 40,000 grams per mole although the molecular weight may range from about 30,000 to about 50,000 grams per mole. The preferred molecular weight of the polyethylene glycol is about 6,000 grams per mole although the molecular weight may be in the range of from about 5,000 to about 6,500 grams per mole. Both PVP and PEG are effective when present in amounts of from about 2% to about 18% by weight of the precipitating reagent. The preferred concentration of PVP is about 6% by weight of the precipitating reagent and the preferred concentration of PEG is about 2.5% by weight of precipitating reagent. For some applications, PEG offers advantages over PVP because PEG is colorless and more heat stable than PVP, thereby lending itself to shipping and prolonged storage.

The combination of polyanion, neutral polymer and buffer of the precipitating reagent allows complete and immediate selective precipitation of low density lipoproteins from human serum, including very low density lipoproteins and chylomicrons, without the addition of metal ions. When the precipitating reagent is incorporated in the preferred assay method according to the invention, a sensitivity of 0.1 mg/dL of high density lipoprotein cholesterol results. The precipitating reagent combination of the invention results in a low final concentration of polyanion, buffer and neutral polymer maximizing compatability with the enzymatic cholesterol assay reagent to provide improved accuracy and reproducibility.

While the precipitating reagent is described with reference to the determination of high density lipoprotein cholesterol, it is to be understood that the concentration of other lipoprotein components such as triglyceride, phospholipids and apo-proteins A, B and C may be determined by performing the suitable assay on the supernatant obtained by the precipitating reagent and method according to the invention.

The preferred method of the present invention for the determination of high density lipoprotein cholesterol includes the following steps and the total test takes less than 30 minutes. The serum specimen and precipitating reagent preferably should be allowed to reach ambient temperature. Equal volumes of the precipitating reagent and serum are mixed together, the preferred volume of each being about 0.50 milliliters. The preferred composition of the precipitating reagent where equal volumes of serum and precipitating reagent are used is:

0.4% by weight Phosphotungstic Acid
0.2 molar MES
2.5% by weight PEG.

This composition together with an equal volume of serum sample optimizes the sensitivity of the procedure while minimizing the sample volume required. Variations of the sample volume while at the same time making appropriate variations in the quantity of reagent added as well as variations in the concentrations of components in the precipitating reagent can be made. For example, the use of automated equipment may require that a more concentrated precipitating reagent be used because of volume limitations of the equipment. However, because of the complex mechanism involved in the precipitation, use of a more concentrated reagent does not necessarily mean that the volume of reagent required to provide optimum results will change by a factor inverse to the concentration change. Relative amounts of the components in the reagent may also change. For example, if it is desired that only 0.1 ml of precipitating reagent is to be added to a 0.5 ml serum sample, the optimum composition of the precipitating reagent is:

2.4% by weight Phosphotungstic Acid
1.0 molar MES, pH 5.20
12% by weight PEG.

In this embodiment the components may be present in a range of Phosphotungstic acid of from about 1.8% to about 3.0% by weight thereof, PEG in the range of from about 6% to about 18% by weight thereof and MES of from about 0.6 molar to about 1.2 molar, pH about 4.8 to about 5.8. Additionally, this formulation may contain ethylenediaminetetraacetic acid in the range of from about 10 millimolar to about 60 millimolar and preferably about 30 millimolar. The effect of ethylenediaminetetraacetic acid will be hereinafter described.

According to the invention, after addition of the precipitating reagent to the serum sample, the components of the precipitating reagent should be present in amounts of about 0.1% to about 0.5% by weight phosphotungstic acid, about 1.0% to about 4.0% by weight neutral polymer and about 0.1 molar to about 0.25 molar organic buffer so that the pH of the resulting mixture is approximately at the isoelectric point of the low density lipoproteins. Optionally, a metal complexing agent, such as ethylenediaminetetraacetic acid, may be incorporated in the precipitating reagent so that after addition of the reagent to the serum sample, the concentration of the metal complexing agent will be from about 1.6 millimolar to about 10 millimolar.

The synergistic combination of components in the precipitating reagent results in complete and immediate precipitation of low density lipoproteins including very low density lipoproteins and chylomicrons at lower concentrations of polyanion and polymer than heretofore accomplished.

Upon addition of the precipitating reagent, serum pH is lowered approximately to the isoelectric point of low density lipoproteins (a pH of approximately 5.7), where the low density lipoprotein molecules have an overall electrical neutrality, thereby facilitating precipitation. At this pH, phosphotungstic acid forms an insoluble complex with low density lipoprotein which can then be separated from the supernatant fraction. The presence of the neutral polymer further promotes the precipitation through an unknown mechanism, which may be through hydrogen bonding or by effectively lowering the ionic strength of the solution, for example. The low concentration of neutral polymer does permit the use of lower concentrations of polyanion than heretofore used in the art and the resulting novel combination provides a precipitating agent that is neither time nor temperature dependent, but yet quantitative. Thus, the use of the preferred precipitating reagent assures immediate and complete separation of high density lipoprotein from other serum lipoproteins at ambient temperature. The resulting precipitate that forms is separated from the supernatant liquid preferably with the assistance of a centrifuge. Most preferably, the sample is centrifuged for about 10 minutes at approximately $750 \times G$. The supernatant liquid or fraction contains the high density lipoproteins and the precipitate contains the low density lipoproteins.

Alternatively, according to the method of the present invention, the amount of high density lipoprotein cholesterol in human serum can be determined without the addition of metal ions by adding the components of the reagent separately, as follows: (a) adjusting the pH of the serum to approximately the low density lipoprotein isoelectric point with an organic buffer; (b) introducing phosphotungstic acid into the serum; (c) introducing a neutral polymer into the serum to form precipitate and supernatant fractions. Thereafter, the resulting precipitate can be separated from the supernatant liquid as aforesaid.

After the low density lipoproteins have been separated from the high density lipoproteins, the supernatant containing the high density lipoproteins is analyzed for cholesterol. While any established method for determination of cholesterol may be used in the cholesterol assay of the supernatant fraction, a particular assay reagent is preferred and the method described herein employs the preferred cholesterol assay reagent hereinafter described. The cholesterol assay reagent is added to the supernatant fraction and contains the following ingredients and quantities: about 0.36 U/Test cholesterol esterase, about 0.40 U/Test cholesterol oxidase, about 100 U/Test peroxidase, about 0.4 milligrams/Test 4-aminoantipyrine and about 6.0 milligrams/test phenol. The The cholesterol assay is based on the following sequence of enzymatic reactions:

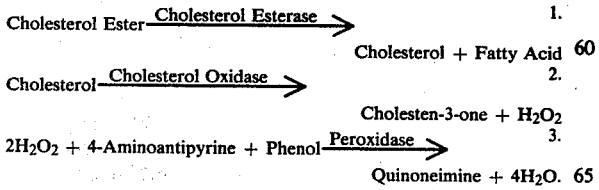

Cholesterol esterase in the cholesterol assay reagent hydrolizes cholesterol esters to cholesterol and free fatty acids. The cholesterol produced from this reaction, plus free cholesterol present in the sample, are oxidized by cholesterol oxidase to form cholesten-3-one and hydrogen peroxide. Peroxidase catalyzes the hydrogen peroxide oxidation of 4-aminoantipyrine with subsequent coupling to phenol. The end product is quinoneimine which has maximum absorbance at 500 nm.

According to the method, the cholesterol assay reagent in introduced into a test tube and warmed to approximately 37° C. 200 $\mu$L of the supernatant fraction is then added, mixed and incubated for about 15 minutes at approximately 37° C. A spectrophotometer calibrated to read absorbance at 500 nm is zeroed using a reagent blank and the absorbance of the sample is then determined. The high density lipoprotein (HDL) cholesterol is determined by the following equation:

$$\frac{\text{(absorbance of sample)}}{\text{(absorbance of reference)}} \times \frac{\text{(cholesterol concentration of reference)}}{} = \text{Concentration of HDL cholesterol in sample}$$

The high density lipoprotein cholesterol assay method shows linearity to 125 mg/dL and sensitivity of 0.1 mg/dL of HDL cholesterol. Samples exceeding 125 mg/dL HDL cholesterol should be diluted and analyzed again. The final reaction product of the cholesterol assay is stable for about 30 minutes when maintained at temperatures between 15° and 30° C.

The concentration of low density lipoprotein cholesterol in a fasting human serum specimen can also be determined when total cholesterol, HDL cholesterol and triglyceride concentrations are known, as set forth by W. T. Friedewald, R. I. Levy, and D. S. Fredrickson, Clin. Chem. 18, 499–502 (1972). A cholesterol assay is run on part of the human serum sample without precipitation of the low density lipoproteins to determine the concentration of total serum cholesterol. The total cholesterol assay is performed in the manner previously described, except that 20 $\mu$L of serum are used instead of 200 $\mu$L of supernatant. Determination of triglyceride can be done by any method known to those skilled in the art.

EXAMPLE 1

The precipitating reagent and method of the invention was evaluated to determine within run reproducibility by conducting precipitation of low density lipoproteins 10 times on a normal serum pool and assaying the supernatants to determine the high density lipoprotein cholesterol concentrations. The precipitating reagent contained about 0.4 percent by weight thereof phosphotongstic acid, about 2.5 percent by weight thereof polyethylene glycol and about 0.2 molar 2-(N-morpholino) ethane sulfonic acid. About 0.50 milileters readers of the precipitating reagent and about 0.50 milileters of serum from the pool were mixed together for each run. The resulting precipitate was separated by centrifuging for about ten minutes at approximately $750 \times G$. To about 200 $\mu$L of supernatant was added the cholesterol assay reagent which consisted of about 0.36 U cholesterol esterase, about 0.40 U cholesterol oxidase, about 100 U peroxidase, about 0.4 milligrams 4-aminoantipyrine and about 6.0 milligrams phenol. The 200 $\mu$L sample of the supernatant fraction was added to the cholesterol assay reagent after warming the reagent to approximately 37° C. The mixture of supernatant and assay reagent was incubated for about 15 minutes at approximately 37° C. A spectrophotometer calibrated to read absorbance at 500 nm was zeroed using a reagent blank and the absorbance of the sample was then determined. The high density lipoprotein cholesterol concentration was determined by the ratio of the absorbance of the sample to the absorbance of a known reference times the absorbance of the reference. The test was repeated ten times and the following results were obtained:

|  | Mean | Std. Dev. | Coef. of Variation (%) |
|---|---|---|---|
| Within Run HDL | 53 mg/dL | 1.0 mg/dL | 1.9 |

EXAMPLE 2

Day-to-day HDL reproducibility of the preferred precipitating reagent and method was determined by conducting precipitation of low density lipoproteins on a normal serum pool for five successive days and assaying the supernatants using the reagents and methods as set forth in Example 1. The following results were obtained:

|  | Mean | Std. Dev. | Coef. of Variation (%) |
|---|---|---|---|
| Day-to-day HDL | 52 mg/dL | 1.6 mg/dL | 3.1 |

According to the invention, the precipitating reagent should be stored at between about 2° and about 30° C. The precipitating reagent should be clear and if a cloudiness is present the reagent may have deteriorated, and therefore, should not be used.

The supernatant obtained after treating serum with the precipitating agent is clear following separation from the precipitate. However, upon standing, a cloudiness develops but does not interfere with the HDL cholesterol assay. The composition of the precipitating reagent may include a low concentration of a metal complexing agent, such as ethylenediaminetetraacetic acid. Inclusion of a metal complexing agent is most advantageous where automated instruments are used to assay the serum because the sampling system could be blocked by a turbid supernatant.

This invention has been described in detail with reference to its preferred embodiments, and many modifications will now be apparent to those skilled in the art and those modifications are intended to be within the scope of the appended claims.

What is claimed is:

1. A precipitating reagent for selectively precipitating low density lipoproteins from human serum which comprises phosphotungstic acid, an organic buffer having a pH buffering range of from about 4.8–6.8 and a concentration of from about 0.2 molar to about 1.2 molar and a neutral polymer selected from the group consisting of polyvinylpyrollidone, polyethylene glycol and poly-N-vinyl-5-methyl-2-oxazolidinone, said phosphotungstic acid and said neutral polymer present in effective amounts for selectively precipitating low density lipoproteins.

2. The precipitating reagent as recited in claim 1 wherein the polyvinylpyrollidone has a molecular weight in the range of from about 30,000 grams per mole to about 50,000 grams per mole and the polyethylene glycol has a molecular weight in the range of from about 5,000 grams per mole to about 6,500 grams per mole.

3. The precipitating reagent as recited in claim 1 wherein at least about 0.2% by weight thereof is phosphotungstic acid.

4. The precipitating reagent as recited in claim 3 wherein the buffer is 2-(N-morpholino) ethane sulfonic acid.

5. A precipitating reagent for selectively precipitating low density lipoproteins from human serum which comprises:
    (a) from about 0.2% to about 3.0% phosphotungstic acid by weight thereof;
    (b) a zwitterionic buffer having a useful pH buffering range of from about 5.2 to about 6.8 and a pKa of about 6.15 at 20° C. present in a concentration of from about 0.2 molar to about 1.2 molar; and
    (c) from about 2.0% to about 18.0% by weight thereof is a neutral polymer selected from the group consisting of polyvinylpyrollidone having a molecular weight of approximately 40,000 grams per mole and polyethylene glycol having a molecular weight of approximately 6,000 grams per mole.

6. The precipitating reagent as recited in claim 5, wherein:
    (a) about 0.4% by weight thereof is phosphotungstic acid;
    (b) the zwitterionic buffer is 2-(N-morpholino) ethane sulfonic acid; and
    (c) the neutral polymer is polyvinylpyrollidone present in a concentration of about 6% by weight thereof.

7. The precipitating reagent as recited in claim 5, wherein:
    (a) about 0.4% by weight thereof is phosphotungstic acid;
    (b) the zwitterionic buffer is 2-(N-morpholino) ethane sulfonic acid; and
    (c) the neutral polymer is polyethylene glycol present in a concentration of about 2.5% by weight thereof.

8. The precipitating reagent as recited in claim 5 further comprising ethylenediaminetetraacetic acid.

9. The precipitating reagent as recited in claim 5 wherein:
    (a) about 2.4% by weight thereof is phosphotungstic acid;
    (b) the zwitterionic buffer is 2-(N-morpholino) ethane sulfonic acid present in a concentration of about 1.0 molar; and
    (c) the neutral polymer is polyethylene glycol present in a concentration of about 2.5% by weight thereof.

10. The precipitating reagent as recited in claim 9 further comprising ethylenediaminetetraacetic acid present in the range of from about 10 millimolar to about 60 millimolar.

11. A method for precipitating low density lipoproteins and determining the amount of high density lipoprotein cholesterol in human serum without the addition of metal ions which comprises adjusting the pH of said serum approximately to the low density lipoprotein isoelectric point with an organic buffer, introducing phosphotungstic acid into said serum and introducing a neutral polymer into said serum, said phosphotungstic acid and said neutral polymer being introduced in said serum in effective amounts for precipitating low density lipoproteins thereby forming precipitate and supernatant fractions, said neutral polymer selected from the group consisting of polyvinylpyrollidone, polyethylene glycol and poly-N-vinyl-5-methyl-2-oxazolidinone, and analyzing the supernatant for high density lipoprotein cholesterol.

12. The method as recited in claim 11 wherein:
(a) the concentration of the organic buffer in the serum is from about 0.1 molar to about 0.25 molar;
(b) the concentration of phosphotungstic acid in the serum is from about 0.1% to about 0.5% by weight thereof;
(c) the concentration of neutral polymer in the serum is from about 1.0% to about 4.0% by weight thereof; and
(d) said concentrations of organic buffer, phosphotungstic acid and neutral polymer being the concentrations in the serum after addition of said organic buffer, said phosphotungstic acid and said neutral polymer.

13. The method as recited in claim 11 wherein said analyzing comprises:
(a) separating said supernatant fraction from said precipitate fraction;
(b) adding to said supernatant fraction a cholesterol assay reagent containing cholesterol esterase, cholesterol oxidase, peroxidase, 4-aminoantipyrine and phenol to form a resulting mixture;
(c) incubating said resulting mixture;
(d) determining the absorbance of said incubated resulting mixture at about 500 nm;
(e) determining the absorbance at about 500 nm at a calibrated reference having a known concentration of cholesterol;
(f) calculating the high density lipoprotein cholesterol concentration of the resulting mixture by multiplying the absorbance of the resulting mixture over the absorbance of the calibrated reference times the cholesterol concentration of the calibrated reference.

14. The method as recited in claim 13 wherein the separation of said supernatant fraction from said precipitate fraction includes centrifugation.

15. The method as recited in claim 13 wherein said cholesterol assay reagent added to said supernatant fraction contains about 0.36 U/cholesterol esterase, about 0.4 U/cholesterol oxidase, about 100 U/oxidase, about 0.4 milligrams 4-aminoantipyrine and about 6.0 milligrams phenol.

16. The method as recited in claim 13 wherein said resulting mixture is incubated at about 37° C. for about 15 minutes.

17. A method for the determination of high density lipoprotein components in human serum selected from the group consisting of triglycerides, phospholipids, apo-proteins A, B and C and cholesterol which comprises:
(a) adjusting the pH of said serum approximately to the low density lipoprotein isoelectric point with an organic buffer;
(b) introducing phosphotungstic acid into said serum;
(c) introducing a neutral polymer into said serum selected from the group consisting of polyvinylpyrollidone, polyethylene glycol and poly-N-vinyl-5-methyl-2-oxazolidinone, said phosphotungstic acid and said neutral polymer present in effective amounts for precipitating low density lipoproteins and forming precipitate and supernatant fractions; and
(d) assaying the supernatant fraction for the specific high density lipoprotein component desired.

18. The method as recited in claim 17 wherein:
(a) the concentration of the organic buffer in the serum is from about 0.1 molar to about 0.25 molar;
(b) the concentration of phosphotungstic acid in the serum is from about 0.1% to about 0.5% by weight thereof;
(c) the concentration of neutral polymer in the serum is from about 1% to about 4% by weight thereof; and
(d) said concentrations of organic buffer, phosphotungstic acid and a neutral polymer being the concentrations in the serum after addition of said organic buffer, said phosphotungstic acid and said neutral polymer.

19. A method for precipitating low density lipoproteins without the addition of metal ions which comprises introducing a reagent into said human serum, said reagent comprising:
(a) from about 0.2% to about 3.0% phosphotungstic acid by weight of said reagent;
(b) a zwitterionic buffer having a useful pH buffering range of from about 5.2 to about 6.8, pKa of about 6.15 at 20° C. present in a concentration in said reagent of from about 0.2 molar to about 1.2 molar;
(c) from about 2.0% to about 18.0% by weight of said reagent of a neutral polymer selected from the group consisting of polyvinylpyrollidone having a molecular weight of about 40,000 and polyethylene glycol having a molecular weight of about 6,000; and
(d) optionally from about 3.2 millimolar to about 60 millimolar ethylenediaminetetraacetic acid, said reagent being introduced into said human serum so that concentration of the reagent components in the combined reagent and human serum is from about 0.1% to about 0.5% by weight phosphotungstic acid; from about 1.0% to about 4.0% by weight neutral polymer; from about 0.1 molar to about 0.25 molar organic buffer; and from about 1.6 millimolar to about 10 millimolar ethylenediaminetetraacetic acid.

20. The method as recited in claim 19 wherein:
(a) the precipitating reagent contains about 0.4% phosphotungstic acid by weight thereof;
(b) the zwitterionic buffer is 2-N-morpholino ethane sulfonic acid; and
(c) the neutral polymer present in the precipitating reagent is polyethylene glycol having a molecular weight of about 6,000 and present in a concentration of about 2.5% by weight thereof.

21. The method as recited in claim 19 wherein the neutral polymer is polyvinylpyrollidone having a molecular weight of about 40,000 and is present in a concentration of about 6% by weight thereof.

22. The method as recited in claim 19 wherein equal volumes of said human serum and said precipitating reagents are utilized.

23. A method for the determination of high density lipoprotein components in human serum selected from the group consisting of triglycerides, phospholipids, apoproteins A, B and C and cholesterol which comprises: introducing a reagent into said human serum, which reagent comprises from about 0.2% to about 3.0% phosphotungstic acid by weight of said reagent, a zwitterionic buffer having a useful pH buffering range of from about 5.2 to about 6.8, a pKa of about 6.15 at 20° C. and present in a concentration of from about 0.2 molar to about 1.2 molar and from about 2.0% to about 18.0% by weight of said reagent of a neutral polymer selected from the group consisting of polyvinylpyrollidone having a molecular weight of about 40,000 and polyethylene glycol having a molecular weight of about 6,000, said reagent being introduced into said serum so that the pH of said serum is approximately at the low density lipoprotein isoelectric point.

24. The method as recited in claim 23 further comprising the addition to the serum of ethylenediaminetetraacetic acid resulting in a concentration in the combined serum and reagent between about 1.6 millimolar and 10 millimolar, said ethylenediaminetetraacedic acid being contained in said reagent.

* * * * *